United States Patent
Wong et al.

(10) Patent No.: US 11,904,032 B2
(45) Date of Patent: Feb. 20, 2024

(54) WEARABLE ARTICLE AND PREPARATION METHOD THEREFOR

(71) Applicant: TOP GLOVE INTERNATIONAL SDN. BHD., Klang (MY)

(72) Inventors: Chong Ban Wong, Klang (MY); Siew Szen Ling, Klang (MY); Soraya Nur Yazid, Klang (MY)

(73) Assignee: TOP GLOVE INTERNATIONAL SDN. BHD., Selangor (MY)

( * ) Notice: Subject to any disclaimer, the term of this patent is extended or adjusted under 35 U.S.C. 154(b) by 0 days.

(21) Appl. No.: 16/953,833

(22) Filed: Nov. 20, 2020

(65) Prior Publication Data
US 2021/0145704 A1    May 20, 2021

(30) Foreign Application Priority Data
Nov. 20, 2019    (MY) .............................. PI2019006812

(51) Int. Cl.
| | | |
|---|---|---|
| *A61K 8/02* | (2006.01) | |
| *A61Q 19/00* | (2006.01) | |
| *A61K 8/34* | (2006.01) | |
| *A61K 8/67* | (2006.01) | |
| *A61K 8/92* | (2006.01) | |
| *A61K 8/42* | (2006.01) | |

(Continued)

(52) U.S. Cl.
CPC ............. *A61K 8/0204* (2013.01); *A41D 31/18* (2019.02); *A61K 8/345* (2013.01); *A61K 8/42* (2013.01); *A61K 8/678* (2013.01); *A61K 8/922* (2013.01); *A61Q 19/007* (2013.01); *A61Q 19/08* (2013.01); *A61K 2800/805* (2013.01)

(58) Field of Classification Search
CPC .......... A61K 8/42; A61K 8/345; A61K 8/678; A61K 8/922; A61K 8/0204; A61K 2800/805; A61Q 19/007; A61Q 19/08; A61L 31/143; A61L 31/08; A41D 31/18
See application file for complete search history.

(56) References Cited

U.S. PATENT DOCUMENTS

| | | | |
|---|---|---|---|
| 8,458,818 B2 * | 6/2013 | Neuser ................. | A61K 36/899 2/169 |
| 10,238,596 B1 * | 3/2019 | Peck ...................... | A61K 8/737 |
| 2008/0260856 A1 * | 10/2008 | Hasbrouck ............. | A61Q 19/04 424/600 |

FOREIGN PATENT DOCUMENTS

| | | |
|---|---|---|
| WO | WO 2004/022117 A1 | 3/2004 |
| WO | WO 2005/036996 A2 | 4/2005 |

OTHER PUBLICATIONS

EP 20208231.9 Extended European Search Report dated Apr. 21, 2020.

* cited by examiner

*Primary Examiner* — Hong Yu
(74) *Attorney, Agent, or Firm* — Alston & Bird LLP (57) ABSTRACT

A wearable article, a moisturizing composition and a method for preparing a wearable article have been disclosed. The wearable article includes at least a layer of a flexible material, wherein the flexible material is an elastomeric material and an inner surface of the layer of flexible material is a coated with a coating formulation comprising 1% to 7% by weight of a moisturizing composition and 93% to 99% by weight of solvent. The moisturizing composition includes 10 to 30% by weight of at least one humectant and 1.0 to 5.4% by weight of at least one antioxidant. Thereby, the present invention reduces transepidermal water loss (TEWL) and promotes skin barrier recovery.

7 Claims, 5 Drawing Sheets

Fig. 1B (51) Int. Cl.
*A61Q 19/08* (2006.01)
*A41D 31/18* (2019.01)

WEARABLE ARTICLE AND PREPARATION METHOD THEREFOR

CROSS-REFERENCE TO RELATED APPLICATIONS

This application claims priority to Malaysia Patent Application No. PI2019006812 filed on Nov. 20, 2019, which is incorporated by reference in its entirety for all purposes.

FIELD OF THE INVENTION

The disclosures made herein relate generally to the field of wearable articles and more particularly to a wearable article, a moisturizing composition and a method for preparing the wearable article therefor for minimizing transepidermal water loss and improving skin hydration.

BACKGROUND OF THE INVENTION

Natural rubber has many desired qualities like elasticity, toughness, impermeability, adhesiveness and electrical resistance, hence it is the most suitable material for wearable articles in many industries. Meanwhile, synthetic rubber is regarded as a better replacement for natural rubber as it has better durability, higher chemical resistance, wider operating temperature range and better weathering properties.

Generally, wearable articles such as gloves, condoms, finger cot and the like are made of latex (natural or synthetic) and to be worn skin tight, which often results in discomfort to users who are wearing such articles for long period. Researchers have tried to coat an inner surface of the wearable articles with additives to improve user experience and comfort. On the contrary, such coatings have resulted in undesirable residues on skin surface which may lead to discomfort and/or allergies.

Some of the manufacturers have attempted to manufacture latex articles, wherein natural extracts are present within the article as one or combination of a polymer, co-polymer and filler of the article. U.S. Pat. No. 6,589,544 B2 discloses a method for manufacturing an aloe vera impregnated article, wherein an elastomeric article is prepared by mixing aloe vera extracts with a latex composition that is used for manufacturing the article. Such article may be successful in reducing user discomfort but mixture of natural extracts with the latex composition may affect the desired qualities of such article, for example, the durability and flexibility.

United States Patent Publication No. 2006/0062815 A1 discloses a therapeutic glove, wherein a coating of cucumber extract and/or glycerin is applied on an inner surface. The coating is capable of soothing the hand without affecting characteristics and functions of the gloves. However, such coating is less effective as compared to oil-based moisturizers.

Hence, there is a need for a wearable article and a preparation method therefor, which improves user experience and skin hydration effect without degrading desired characteristics of such article.

SUMMARY OF THE INVENTION

In accordance with a first aspect of the present invention, a moisturizing composition for coating a wearable article comprises:
i. 10 to 30% by weight of at least one humectant; and
ii. 1.0 to 5.4% by weight of at least one antioxidant.

Further, the moisturizing composition comprises 10 to 20% by weight of at least one emollient.

According to the first aspect, the humectant is selected from glycerin, glycerol, polyhydric alcohol and mixtures thereof. The antioxidant is selected from vitamin E, tocopheryl acetate, a-tocopheryl acetate and mixtures thereof. The emollient is selected from sweet almond oil (*prunus amygdalus dulcis*), ceramide, shea butter and jojoba oil.

According to a second aspect of the present invention, a wearable article having its inner surface of the layer of flexible material coated with a coating formulation has been disclosed, wherein the wearable article is prepared by forming at least a layer of flexible material. The flexible material is an elastomeric material and the coating formulation comprises 1 to 7% by weight of the moisturizing composition and 93 to 99% by weight of solvent. Preferably, the coating formulation comprises 2.5 to 3.5% by weight of the moisturizing composition and 96.5 to 97.5% by weight of solvent, more preferably 3% by weight of the moisturizing composition and 97% by weight of solvent. The moisturizing composition includes: 10 to 30% by weight of at least one humectant; 1.0 to 5.4% by weight of at least one antioxidant. The moisturizing composition can also include 10 to 20% by weight of at least one emollient.

In accordance with a third aspect of the present invention, a method for preparing a wearable article is disclosed. The method comprises the steps of forming at least a layer of flexible material; coating an inner surface of the layer of flexible material with a coating formulation; and drying the resultant coating for obtaining the wearable article.

Typically, the step of coating the layer of flexible material with a coating formulation includes diluting 1 to 7% by weight of the moisturizing composition in 93 to 99% by weight of solvent preferably water. Preferably, the coating formulation comprises 2.5 to 3.5% by weight of the moisturizing composition and 96.5 to 97.5% by weight of solvent, more preferably 3% by weight of the moisturizing composition and 97% by weight of solvent preferably water, wherein the moisturizing composition comprises: 10 to 30% by weight of at least one humectant and 1.0 to 5.4% by weight of at least one antioxidant.

Additionally, the moisturizing composition comprises 10 to 20% by weight of at least one emollient.

Preferably, the step of coating the layer of flexible material with the coating formulation includes spraying the coating formulation on the layer of flexible material, wherein temperature of the coating formulation is maintained in the range of 45 to 60° C. and the layer of flexible material is sprayed for a period of 1 to 5 seconds.

Alternatively, the step of coating the layer of flexible material with the coating formulation includes dipping the layer of flexible material into the coating formulation, wherein temperature of the coating formulation is maintained in the range of 50 to 70° C. and the layer of flexible material is dipped in the coating formulation for a period of 5 to 15 seconds.

Still further, the step of drying the resultant coating is carried out at a temperature of 90 to 150° C. for a period of 120 to 300 seconds.

BRIEF DESCRIPTION OF THE ACCOMPANYING DRAWINGS

The present invention will be fully understood from the detailed description given herein below and the accompanying drawings which are given by way of illustration only, and thus are not limitative of the present invention, wherein.

In the appended drawings.

DETAILED DESCRIPTION OF THE INVENTION

Detailed description of preferred embodiments of the present invention is disclosed herein. It should be understood, however, that the embodiments are merely exemplary of the present invention, which may be embodied in various forms. Therefore, the details disclosed herein are not to be interpreted as limiting, but merely as the basis for the claims and for teaching one skilled in the art of the invention. The numerical data or ranges used in the specification are not to be construed as limiting. The following detailed description of the preferred embodiments will now be described in accordance with the attached drawings, either individually or in combination.

Various terms as used herein are defined below. To the extent a term used in a claim is not defined below, it should be given the broadest definition persons in the pertinent art have given that term as reflected in printed publications and issued patents at the time of filing.

Definitions

Wearable article—Any product that is wearable by a user and is in contact with the user's skin during usage. It includes but not limited to gloves, condom, finger cot, dental dam, exercise band, wearable medical device and the like.

Composition—A mixture of two or more chemical elements or compounds. It may be in the form of powder, liquid, emulsion, dispersion, solution, colloid, suspension, foam, gel and the like.

Additive—An additional component or chemical element added to a composition merely for improving or preserving a product resulting from the composition.

Coating—A thin film uniformly deposited over a surface for covering the surface.

Latex—A stable dispersion of polymer microparticles in an aqueous medium. It may be naturally available or artificially made by polymerizing a monomer that has been stabilized with surfactants.

The present invention relates to a wearable article, a moisturizing composition and a method for preparing the wearable article therefor. The wearable article comprises at least a layer of flexible material and a coating formulation coated over an inner surface of the layer of flexible material, which provides long-lasting hydration for a user by reducing transepidermal water loss (TEWL) and promoting skin barrier recovery without compromising elasticity and other desired qualities of the wearable article. By this way, the wearable article prepared in accordance with the present invention improves user experience.

Figures 1A, 1B:
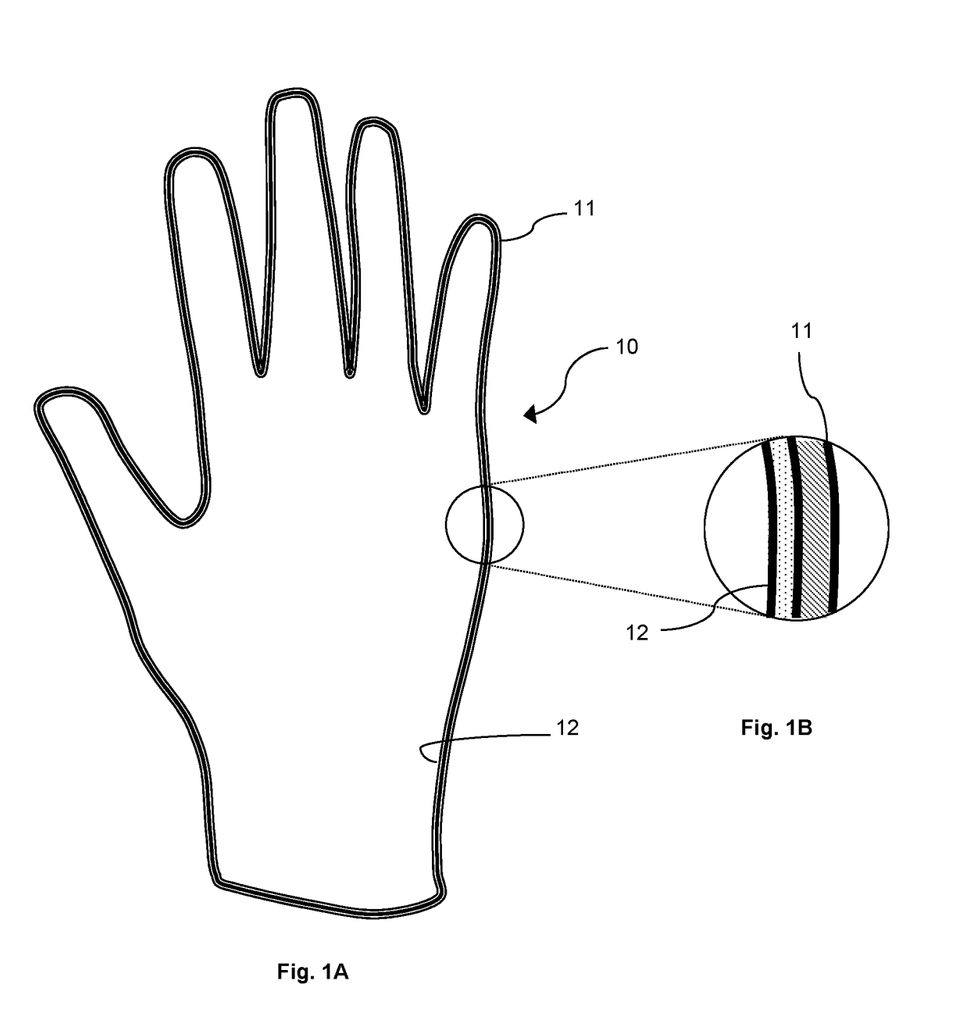
FIG. 1A shows a front view of the wearable article, in accordance with the exemplary embodiment of the present invention.
FIG. 1B shows an enlarged cross-sectional view of a portion of the wearable article, in accordance with the exemplary embodiment of the present invention.

Referring to the accompanying drawings, FIG. 1A shows a front view of the wearable article, in accordance with the exemplary embodiment of the present invention. The wearable article (10) comprises at least a layer of a flexible material (11) and a coating formulation (12) over an inner surface of the layer of flexible material (11). In a preferred embodiment, the flexible material is an elastomeric material or a latex e.g. acrylonitrile butadiene copolymer (NBR) latex. Alternatively, the latex is polychloroprene (CR) latex, polyurethane (PU) latex, polyisoprene (PI) latex or any other conventional synthetic latex. In an alternate embodiment, the flexible material may be natural latex, synthetic latex, fabric, plastics or any combination thereof.

The coating formulation (12) is coated over an inner surface of the layer of flexible material (11), as in FIG. 1B, such that the coating formulation (12) comes in contact with a skin surface when a user wears the article (10). The dried coating formulation (12) forms a thin film covering the inner surface of the layer of flexible material (11), wherein the coating formulation (12) is coated over the layer of flexible material (11), then the wearable article (10) is turned inside out to be as shown in FIG. 1A.

The coating formulation (12) includes 1 to 7% by weight of a moisturizing composition diluted in 93 to 99% by weight of a solvent, preferably water. Preferably, the coating formulation comprises 2.5 to 3.5% by weight of the moisturizing composition diluted in 96.5 to 97.5% by weight of solvent, preferably water. Typically, 3% by weight of a moisturizing composition diluted in 97% by weight of a solvent, preferably water. According to the present invention, the coating formulation, in the form of a lotion, is applied over the layer of flexible material (11).

According to the invention, the moisturizing composition includes:

i. 10 to 30% by weight of at least one humectant; and
ii. 1.0 to 5.4% by weight of at least one antioxidant.

Further, the moisturizing composition includes 10 to 20% by weight of at least one emollient.

Still further, the moisturizing composition includes remaining components such as emulsifiers, a chelating agent and a thickener.

Preferably, the moisturizing composition includes 15 to 20% by weight of humectant and 1.5 to 3.0% by weight of antioxidant.

Typically, the moisturizing composition includes 18% by weight of humectant and 2.0% by weight of antioxidant.

Additionally, the moisturizing composition includes 12 to 15% by weight of emollient. Typically, 13% by weight of emollient.

The humectant is selected from glycerin, glycerol, polyhydric alcohol and mixtures thereof. Preferably, the humectant is glycerin.

The emollient is selected from sweet almond oil (*prunus amygdalus dulcis*), ceramide, shea butter and jojoba oil. Preferably, the emollient is sweet almond oil (*prunus amygdalus dulcis*).

The antioxidant is selected from vitamin E, tocopheryl acetate, a-tocopheryl acetate and mixtures thereof. Preferably, the antioxidant is vitamin E.

The humectant attracts water molecules from the layers of the skin and from the environment to rehydrate the skin surface. The emollient smoothens the skin surface by filling in cracks between skin cells, thus making the skin surface softer.

The antioxidant protects the skin cells against effects of free radicals. By this way, the wearable article prepared in accordance with the present invention reduces transepidermal water loss (TEWL) and promotes skin barrier recovery.

A method for preparing the wearable article will now be explained in accordance with the exemplary embodiment of the present invention. The method typically comprises the steps of: cleaning a former, coating a surface of the former with a coagulant by dipping the former into a coagulant tank, then heating the former in a coagulant oven. The heated former is dipped into a first latex tank, such that the latex is uniformly distributed over the surface coated with the coagulant, then the former is heated in a first latex oven to dry the latex. Further, the former is dipped into a second latex tank and heated in a second latex oven to form another single latex layer, wherein a volume of the two latex tanks is same or different.

The latex layer is pre-leached to remove hydrophilic material from the latex layer and then beaded. The beaded latex layer is heated in a main oven and then chlorinated to harden the surface of the latex layer. The hardened latex layer is post-leached to form the layer of flexible material (11, as in FIG. 1A). The coating (12, as in FIG. 1A) is formed by coating an inner surface of the layer of flexible material (11) with a coating formulation comprising a moisturizing composition by means of spraying. Alternatively, the coating process may also be accomplished by dipping the layer of flexible material (11) into a tank containing a solution comprising the coating formulation or by any other means that enables uniform coating over the layer of flexible material (11). The coating formulation includes 3% of the moisturizing composition that is diluted in 97% by weight of a solvent, preferably water.

Finally, the resultant coating of the wearable article is dried by heating in a final drying oven and then the wearable article is turned inside out to obtain the wearable article (10, as in FIG. 1A), such that the coating (12) forms an interior surface of the wearable article (10), while the layer of flexible material (11) forms an exterior surface of the wearable article (10). Alternatively, the wearable article (10) may also be prepared by forming the layer of flexible material (11) by means of any conventional process for preparing a latex based article or elastomeric article followed by the coating process and the drying process.

The coating process and the drying process are carried out under specific conditions given in Table 1 below. By this way, the present invention enables applying an oil-based composition as a moisturizing layer to the wearable article. It is to be understood that the above preparing conditions are merely for explaining different embodiments of the present invention.

TABLE 1

Physical parameters of the coating and drying processes

| No. | Process | | Preferred range of physical parameters | Working range of physical parameters |
|---|---|---|---|---|
| 1. | Coating | Spraying | Temperature: 50-55° C. Time: 2-3 seconds | Temperature: 45-60° C. Time: 1-5 seconds |
| | | Dipping | Temperature: 55-65° C. Time: 6-10 seconds | Temperature: 50-70° C. Time: 5-15 seconds |
| 2. | Drying | | Temperature: 100-120° C. Time: 180-240 seconds | Temperature: 90-150° C. Time: 120-300 seconds |

Despite the temperatures used for drying the coating is high which is in the range of 90 to 150° C., the coating withstands high temperatures without affecting the benefits provided by the coating which are to reduce transepidermal water loss (TEWL) and promote skin barrier recovery without compromising elasticity and other desired qualities of the wearable article. Hence, the wearable article provides a long-lasting hydration effect for a user wearing the article and improves user experience.

FIG. 2A-2F are graphical representations showing performance results based on tests conducted on one or more conventional glove samples and the wearable article prepared in accordance with the present invention. In reference to FIG. 2A-2E, the wearable article prepared in accordance with the present invention was tested for different parameters and compared with two conventional glove samples. A first conventional glove sample was coated with a layer of aloe vera and second conventional glove sample was coated with a layer of colloidal oatmeal. Meanwhile, in reference to FIG. 2F, the wearable article prepared in accordance with the present invention was tested for different parameters and compared with conventional glove sample wherein the conventional glove sample is non-coated nitrile glove. The comparison results are detailed in the following sections.

Assessment of Short-Term Skin Hydration Effect

Figure 2A:
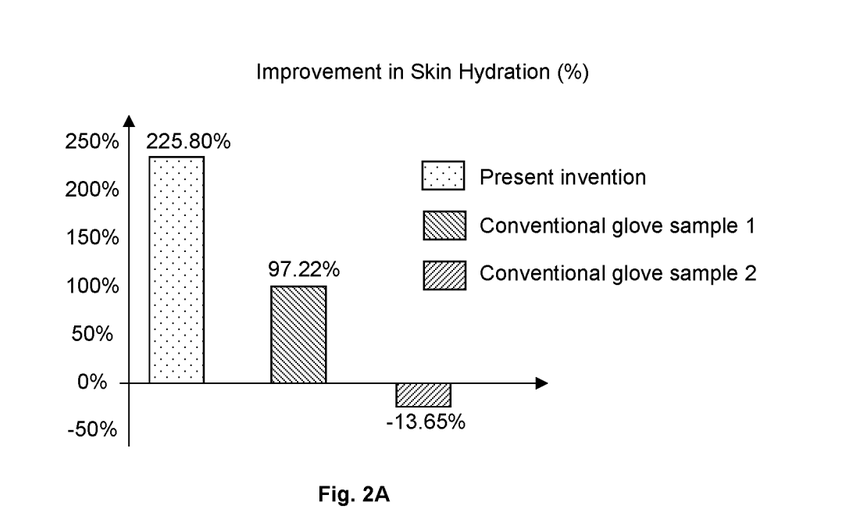
FIGS. 2A-2F are graphical representations showing performance results based on tests conducted on one or more conventional glove samples and the wearable article prepared in accordance with the present invention.

The conventional glove samples and the wearable article prepared in accordance with the present invention were tested with a set of 20 healthy volunteers enrolling in a 60-minute study in Klang, Malaysia. During the study, all volunteers were made to wear the conventional glove samples and the wearable article prepared in accordance with the present invention for 60 minutes in a room with controlled room temperature (24 to 25° C.) and humidity (~40%). FIG. 2A shows a graphical representation of the test results of this study. A measurement of skin hydration for a non-coated nitrile glove served as a baseline measurement (0%) of this study. The measurement was conducted using DermaLab® USB with a skin hydration probe. A total of 4 points were measured at the palm side and rear side of the hand. An average value was calculated using these 4 points of measurement for the wearable article prepared in accordance with the present invention as well as the conventional glove samples. The wearable article prepared in accordance with the present invention exhibited better hydration (225.80%) as compared to conventional glove samples (97.22% and −13.65%).

Assessment of Long-Term Skin Hydration Effect

Figure 2B:
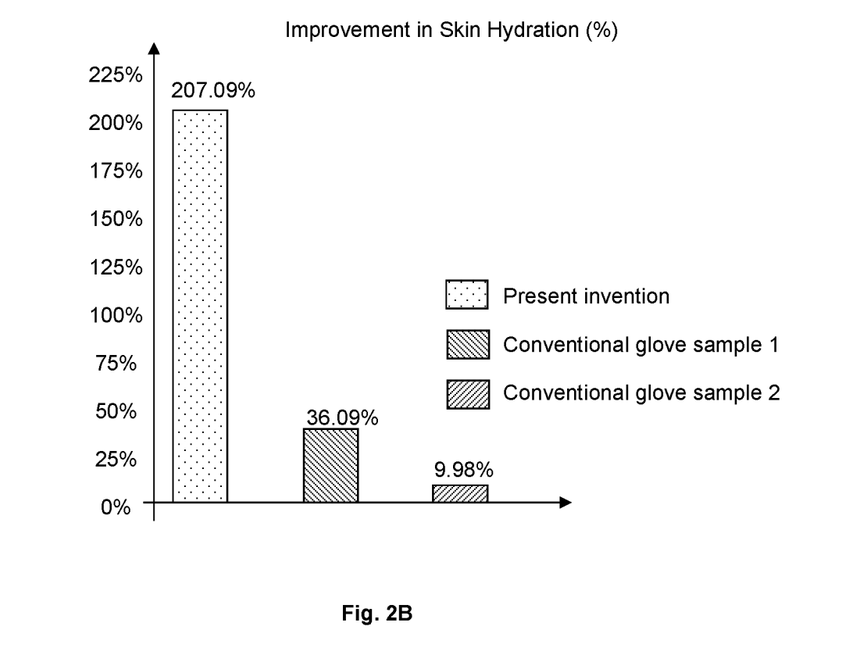

The conventional glove samples and the wearable article prepared in accordance with the present invention were tested with a set of 30 healthy volunteers enrolling in a 14-day study. During the study, all volunteers were made to wear the wearable article prepared according to the embodiments of the present invention on one hand and one of the conventional glove samples on the other hand for 14 days at a rate of 8 hours per day. While wearing, the volunteers were made to stay in a room with controlled room temperature (24 to 25° C.) and humidity (~40%). FIG. 2B shows a graphical representation of the test results of this study. A measurement of skin hydration for a non-coated nitrile glove served as a baseline measurement (0%) of this study. The wearable article prepared in accordance with the present invention exhibited better hydration (207.09%) as compared to conventional glove samples (36.09% and 9.98%).

Assessment on Skin Hydration Test after Drying at High Temperature

Figure 2C:
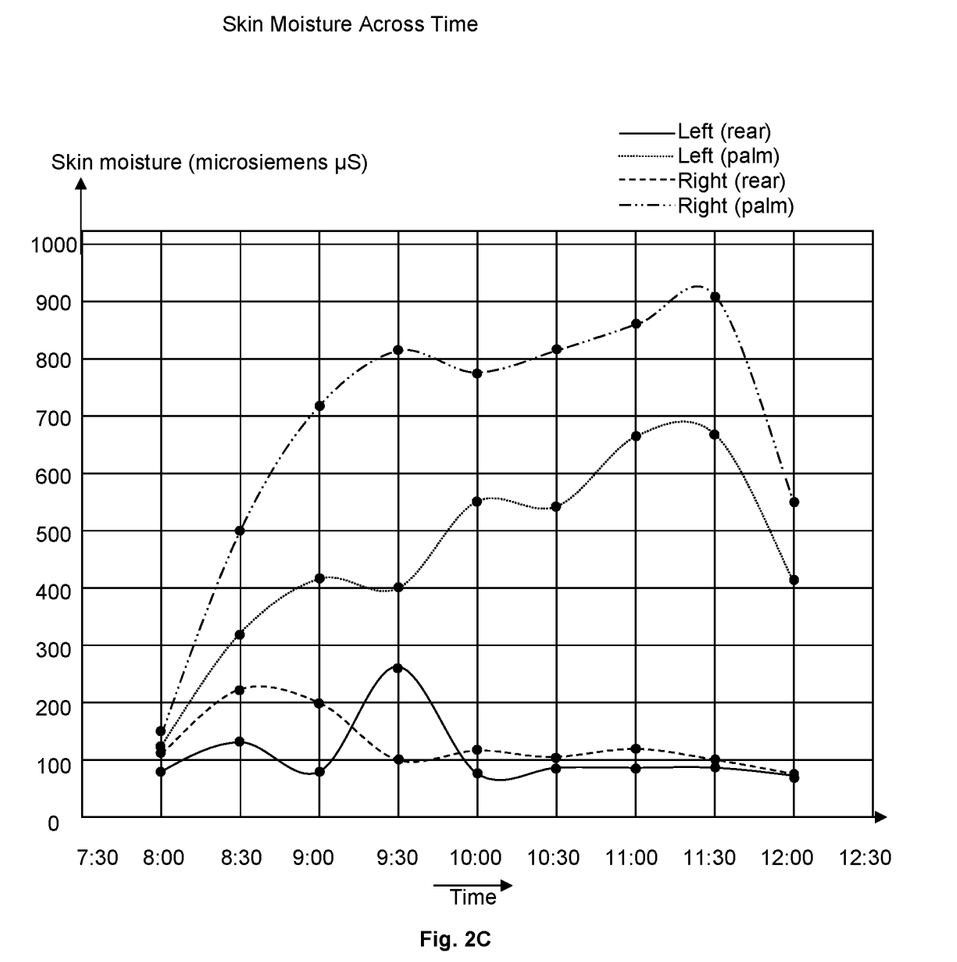

Each volunteer was made to wear the wearable article prepared according to the embodiments of the present invention on right hand and one of the conventional glove samples on left hand for a period of 4 hours. Skin hydration was measured using a scalar moisture meter on palm side and rear side of both hands at every half hour mark to observe the changes in skin hydration over the duration of wear. FIG.

2C shows a graphical representation of the test results of this study. The study results showed that a dried coating on wearable article as proposed in the present invention can withstand high temperature from 50 to 150° C. while still providing its chemical properties i.e. skin hydration effect on the volunteers.

Assessment of Short-Term Skin Barrier Effect

Figure 2D:
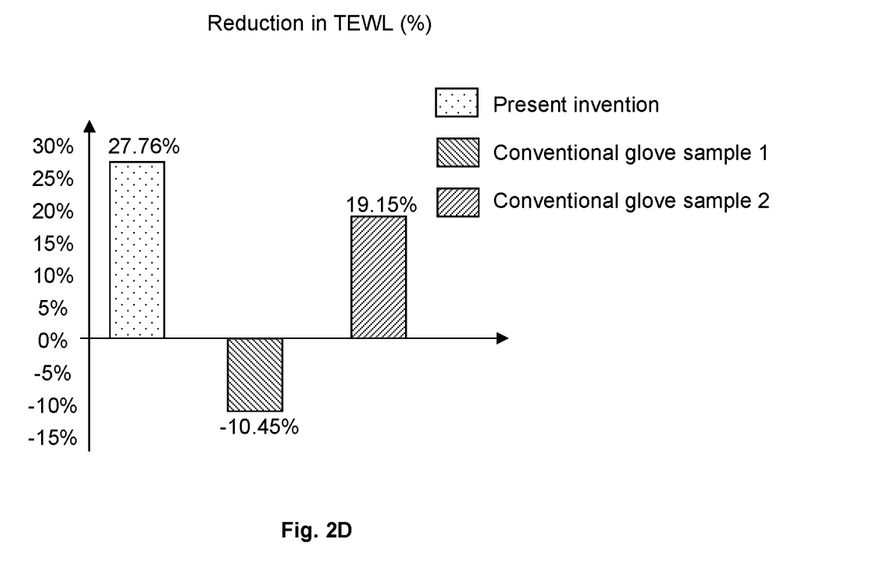

The conventional glove samples and the wearable article prepared in accordance with the present invention were tested with a set of 20 healthy volunteers enrolling in a 60-minute study in Klang, Malaysia. During the study, all volunteers were made to wear the conventional glove samples and the wearable article prepared in accordance with the present invention for 60 minutes in a room with controlled room temperature (24 to 25° C.) and humidity (~40%). FIG. 2D shows a graphical representation of the test results of this study. A measurement of transepidermal water loss (TEWL) for a non-coated nitrile glove served as a baseline measurement (0%) of this study. The measurement was conducted using DermaLab® USB with a TEWL probe. A total of 4 points were measured at the palm side and rear side of the hand. An average value was then calculated using these 4 points of measurement for the wearable article prepared in accordance with the present invention as well as the conventional glove samples. The wearable article prepared in accordance with the present invention exhibited a maximum reduction (27.76%) in water evaporation as compared to conventional glove samples (19.15% and −10.45%).

Assessment of Long-Term Skin Barrier Effect

Figure 2E:
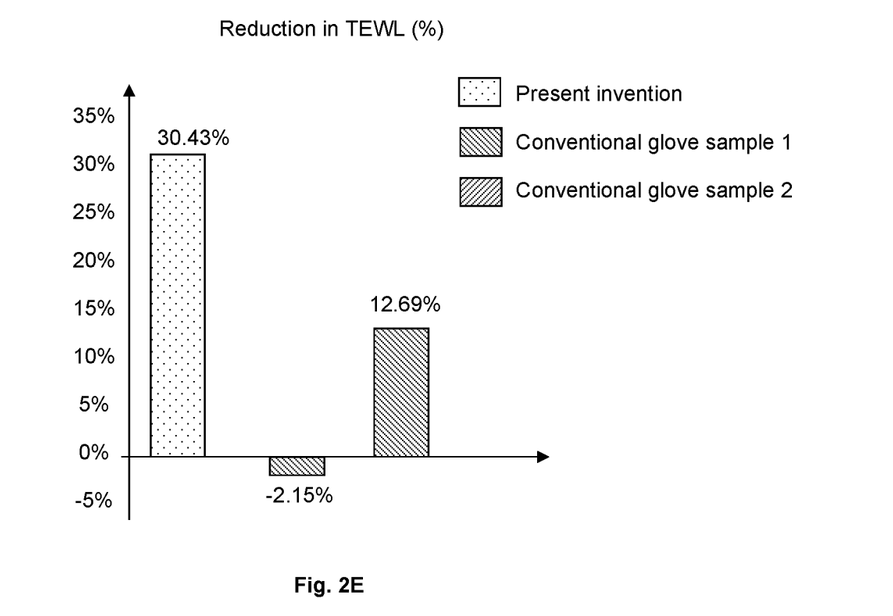

The conventional glove samples and the wearable article prepared in accordance with the present invention were tested with a set of 30 healthy volunteers enrolling in a 14-day study. During the study, all volunteers were made to wear the wearable article prepared according to the embodiments of the present invention on one hand and one of the conventional glove samples on the other hand for 14 days at a rate of 8 hours per day. While wearing, the volunteers were made to stay in a room with controlled room temperature (24 to 25° C.) and humidity (~40%). FIG. 2E shows a graphical representation of the test results of this study. A measurement of TEWL for a non-coated nitrile glove served as a baseline measurement (0%) of this study. The wearable article prepared in accordance with the present invention exhibited a maximum reduction (30.43%) in water evaporation as compared to conventional glove samples (12.69% and −2.15%).

Assessment of Anti-Wrinkle Effect

The conventional glove samples and the wearable article prepared in accordance with the present invention were tested for a depth of wrinkles on volunteers' hand at different time periods during a 12-day study. During the study, all volunteers were made to wear the wearable article prepared in accordance with the present invention on one hand and conventional glove sample on the other hand for 12 days at a rate of 8 hours per day. A microcamera was used for measuring the wrinkle depths at the same region on the volunteers' hand for each glove sample. The measurements were taken at T0—before using the glove sample on day 1;
T1—after using the glove sample for 120 minutes on day 1;
T2—after using the glove sample for 30 minutes on day 3;
T3—after using the glove sample for 60 minutes on day 3;
T4—before using the glove sample on day 8; and
T5—after using the glove sample for 120 minutes on day 12.

Figure 2F:
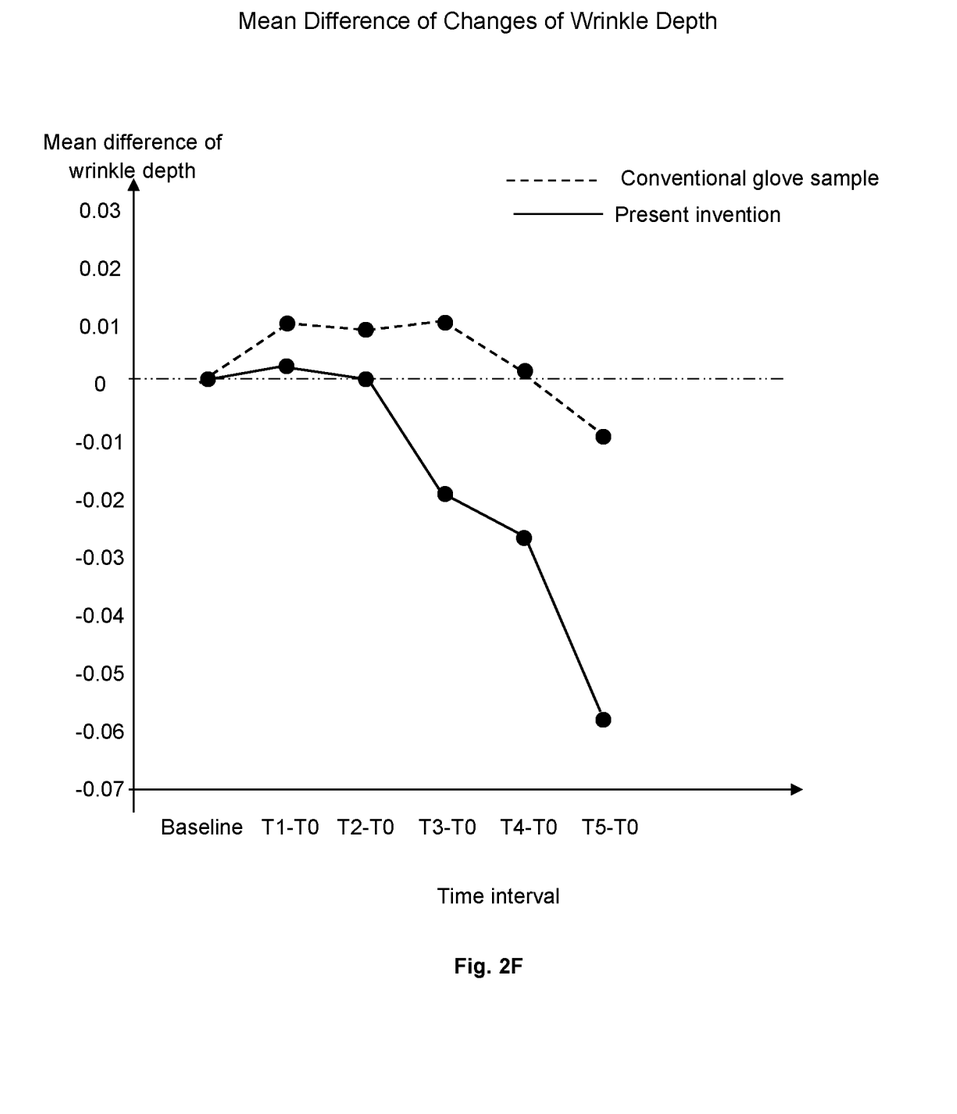

A mean difference of changes in wrinkle depths measured during the abovementioned time intervals are plotted as in FIG. 2F. This study showed that the wearable article prepared in accordance with the present invention exhibits better anti-wrinkle effect as compared to the conventional glove sample from day 1 to day 12.

Thus, from the above listed test results, it is clear that the wearable article prepared in accordance with the present invention is very effective in providing long-lasting hydration for a user by applying an oil-based composition as a moisturizing layer to the interior surface of the wearable article. Thus, the wearable article prepared in accordance with the present invention is very effective in reducing TEWL and promoting skin barrier recovery without compromising elasticity and other desired qualities of the wearable article. By this way, the wearable article prepared in accordance with the present invention improves user experience.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including" and "having" are inclusive and therefore specify the presence of stated features, integers, steps, operations, elements and/or components, but do not preclude the presence or addition of one or more other features, integers, steps, operations, elements, components and/or groups thereof.

The method, steps, processes and operations described herein are not to be construed as necessarily requiring their performance in the particular order discussed or illustrated, unless specifically identified as an order of performance. It is also to be understood that additional or alternative steps may be employed. The use of the expression "at least" or "at least one" suggests the use of one or more elements, as the use may be in one of the embodiments to achieve one or more of the desired objects or results.

The invention claimed is:

1. A moisturizing composition for coating a wearable article, consisting of:
    i. 0.1 to 2.1% by weight of at least one humectant, wherein the humectant is selected from the group consisting of glycerin, glycerol, polyhydric alcohol and mixtures thereof;
    ii. 0.01 to 0.378% by weight of at least one antioxidant, wherein the antioxidant is selected from the group consisting of vitamin E, tocopheryl acetate, a-tocopheryl acetate and mixtures thereof;
    iii. 0.1 to 1.4% by weight of at least one emollient, wherein the emollient is selected from the group consisting of sweet almond oil (*prunus amygdalus dulcis*), ceramide, shea butter and jojoba oil and
    iv. water.

2. The moisturizing composition as claimed in claim 1, wherein the moisturizing composition comprises 0.15 to 1.4% by weight of at least one humectant.

3. The moisturizing composition as claimed in claim 1, wherein the moisturizing composition comprises 0.015 to 0.21% by weight of at least one antioxidant.

4. The moisturizing composition as claimed in claim 1, wherein the moisturizing composition comprises 0.18-1.26% by weight of at least one humectant.

5. The moisturizing composition as claimed in claim 1 wherein the moisturizing composition comprises 0.02-0.14% by weight of at least one antioxidant.

6. The moisturizing composition as claimed in claim 1, wherein the moisturizing composition comprises 0.12-1.05% by weight of at least one emollient.

7. The moisturizing composition as claimed in claim 1, wherein the moisturizing composition comprises 0.13-0.91% by weight of at least one emollient.

\* \* \* \* \*